United States Patent
Morone et al.

(10) Patent No.: US 11,130,873 B2
(45) Date of Patent: Sep. 28, 2021

(54) MULTIFUNCTIONAL POLYMERIC PHOTOINITIATORS

(71) Applicant: IGM GROUP BV, Waalwijk (NL)

(72) Inventors: Marika Morone, Lipomo (IT); Gabriele Norcini, Comabbio (IT); Vincenzo Razzano, Siena (IT)

(73) Assignee: IGW GROUP BV, Waalwijk (NL)

( * ) Notice: Subject to any disclaimer, the term of this patent is extended or adjusted under 35 U.S.C. 154(b) by 99 days.

(21) Appl. No.: 16/637,050

(22) PCT Filed: Aug. 3, 2018

(86) PCT No.: PCT/IB2018/055856
§ 371 (c)(1),
(2) Date: Feb. 6, 2020

(87) PCT Pub. No.: WO2019/030631
PCT Pub. Date: Feb. 14, 2019

(65) Prior Publication Data
US 2020/0239715 A1 Jul. 30, 2020

Related U.S. Application Data

(60) Provisional application No. 62/542,990, filed on Aug. 9, 2017.

(51) Int. Cl.
*C08F 2/50* (2006.01)
*C09D 11/10* (2014.01)
*C09D 11/101* (2014.01)
*C07D 311/16* (2006.01)
*C09D 11/38* (2014.01)

(52) U.S. Cl.
CPC .......... *C09D 11/101* (2013.01); *C07D 311/16* (2013.01); *C09D 11/38* (2013.01)

(58) Field of Classification Search
CPC .......... C09D 11/38; C09D 11/101; C08F 2/48; C08F 2/50; C07D 311/16
USPC .................................. 522/63, 113, 120, 121
See application file for complete search history.

(56) References Cited

U.S. PATENT DOCUMENTS 9,382,433 B2 * 7/2016 Rowatt ................ C09D 11/101

FOREIGN PATENT DOCUMENTS

| KR | 20090108154 | 10/2009 |
| WO | 2005014677 | 2/2005 |
| WO | 2014018826 | 1/2014 |
| WO | 2014063997 | 5/2014 |

OTHER PUBLICATIONS

International serch report and writen opinion issued by the EPO for PCT/IB2018/055856 dated Nov. 20, 2018.

* cited by examiner

*Primary Examiner* — Sanza L. McClendon

(57) ABSTRACT

The present invention relates to novel compounds based on 3-ketocoumarins, which are useful as photoinitiators and sensitizer and to compositions thereof. More particularly, the novel compounds comprise a polyhydroxy polymeric core, which is chemically bonded to 3-ketocoumarin derivatives.

14 Claims, No Drawings

MULTIFUNCTIONAL POLYMERIC PHOTOINITIATORS

This application is a U.S. national stage of PCT/IB2018/055856 filed on 3 Aug. 2018, which claims priority to and the benefit of the content of U.S. Provisional Application Ser. No. 62/542,990, filed 9 Aug. 2017, the contents of which are incorporated herein by reference in their entireties.

The present invention relates to novel compounds based on 3-ketocoumarins, which are useful as photoinitiators and sensitizer and to compositions thereof. More particularly, the novel compounds comprise a polyhydroxy polymeric core, which is chemically bonded to 3-ketocoumarin derivatives.

TECHNICAL BACKGROUND

Photoinitiators used in radiation curable coatings need to have high cure speed, in particular good surface curing, low odour, good solubility and low yellowing properties.

Among the light radiation sources used in this field, light emitting diodes (LED), a semiconductor light source, have been the subject of significant development over the past few years because of the advantages of low temperature operation and extremely long life in comparison with conventional medium pressure mercury arc curing lamps. LED lamps are advantageous because of the inherently small size of LED units, their longer lifetime, their robustness and their ability to be easily engineered, for example into commercial printing systems.

When using LED lamps to photocure inks and coatings, it is necessary to use selected photoinitiator systems that are tuned to the wavelength of said light source. While Mercury arc lamps typically have a polychromatic emission spectrum, emitting light in all regions of the UV-visible spectrum from 200 to 450 nm, LED lamps usually have only a single emission band in the range 365-420 nm.

Photoinitiators, absorbing in the region between 365 nm and 420 nm, are thus required to make full use of the recent development of LEDs with increasing power. Moreover, since high concentration of photoactive substance are usually required for LED applications, the photoinitiators should have a high compatibility with the photopolymerizable system. Thioxanthones, such as isopropyl thioxanthone (ITX) and its derivatives, and acyl phosphine oxides are photoinitiators commonly used in this field.

Unfortunately, the thioxanthone derivatives commonly used both as photoinitiators and sensitizers are prone to yellowing upon exposure, thereby forming degradation products with limited stability. As a result, the original yellowing can shift unpredictably upon storage. Especially in imaging, e.g. inkjet printing, this unstable yellowing behavior makes quite difficult the control of the image tone in the final image.

Acyl phosphine oxides initiators, on the other hand, result in medium volatile aldehyde type of degradation products, producing a background smell of the cured coatings or the printed.

In the last years, many works were published on 3-ketocoumarins useful as photoinitiators for radiation curable coatings.

In particular, in WO2014/063997 new 3-ketocoumarins with improved reactivity and low yellowing are described, but among the high reactivity and the low yellowing these compounds show also a very pour solubility in is coating formulations.

An improvement in solubility was described in WO2014/018826 (Sun Chemical Corporation), but the reactivity at 395 nm still remained an issue. Moreover when radiation curable compositions are used for food packaging, toys or dental applications, the amount of residues or degradation products of photoinitiators able to diffuse out of the cured coating into the surrounding medium (migration) it's a critical issue. Low molecular weight compounds are usually not completely built into the polymer network and are prone to be extracted or to diffuse out of the cured composition. Therefore, there is a continuous effort to design photoinitiators having a reduced tendency to migrate out or to be extracted of the cured composition.

One approach to overcome these problems is to use photoinitiators which contain an ethylenically unsaturated moiety. For example, WO2005014677 (Ciba) and KR20090108154 (LG Chemical Ltd.) disclose derivatives of 3-ketocoumarins with a (meth)acrylated function. The ethylenically unsaturated group enables the photoinitiator to be incorporate into the polymeric structure, during the curing process, but reduces also the mobility of the formed radicals and, as a consequence, their activity An alternative approach is to use photoinitiators of increased molecular size, which have an increased probability to be blocked into the cured products, resulting in reduced levels of migratable and/or extractable degradation products. This solution is disclosed in WO2014/018826.

However, these photoinitiators have a strong tendency to lose reactivity. Hence, often considerable amounts of these photoinitiators are required in order to reach the desired curing speed, thereby also increasing the viscosity to an undesirable level for a great number of applications of radiation curable compositions, such as e.g. inkjet printing. Moreover, above a concentration of 10-12% non-acrylate functional materials either start to behave as plasticizers or just reduce the crosslink density of the cured film to a point where its mechanical properties are impaired.

For the above reasons, there is still a need for novel photoinitiators having improved interactions with radiation-curable coating systems.

OBJECTS OF THE INVENTION

It is a first object of the invention to provide novel multifunctional compounds based on 3-ketocoumarins which have good solubility, high reactivity, low yellowing and give cured products which have extremely low odor and do not generate degradation products with tendency to migrate and to be extracted.

It is further object of the invention to provide the use of said novel compounds as photoinitiators and sensitizers in ultraviolet-light induced cationic curing.

It is a further object of the invention to provide a photocuring process which involves the use of said novel compounds as well as compositions and inks comprising them.

These and other objects are achieved by the invention which provides the novel compounds according to claims 1 to 8, their use as photoinitiators of claims 10 to 14 and as sensitizer of claims 21 and 22, a photocuring process according to claims 16 to 19, compositions, inks and coatings of claim 15 and articles according to claim 20.

DESCRIPTION OF THE INVENTION

According to one of its aspects, a subject-matter of the invention is a compound of Formula (I)

wherein

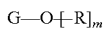   (I)

wherein
G is a monomeric, oligomeric and polymeric polyhydroxylated and/or polyalcoxylated moiety;
R is

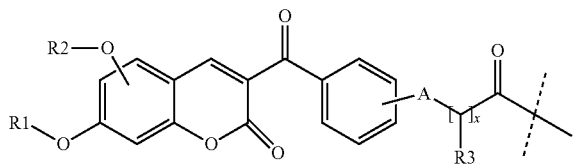

wherein
the dotted line indicates the bond by which R is linked to the oxygen atom;
m is an integer number from 2 to 8;
x is an integer number from 0 to 10, when x is 0 then A is directly linked to the carbonyl group;
each A represents, independently from each other, $CHR_3$, O, S, $NR_4$ wherein $R_4$ is an alkyl $C_1$-$C_6$ group;
each $R_1$, $R_2$ and $R_3$ represents, independently from each other, a group selected from hydrogen, substituted or unsubstituted aryl or heteroaryl; $C_5$-$C_6$ cycloalkyl; $C_1$-$C_{12}$ alkyl optionally substituted with —SH, —N(alkyl $C_1$-$C_6$)$_2$, piperidino, morpholino, piperazino, —OH, —O(alkyl $C_1$-$C_{12}$) and —COOH, or $CH_3$—$C_{12}H_{25}$; alkyl alkoxy with the proviso that the photoinitiators of Formula (I) do not contain any photocurable ethylenically unsaturated groups.

Preferably, in Formula (I), m is from 3 to 6 and more preferably 3 to 5.

Preferably, in Formula (I), n is from 1 to 4 in formula I n is no more present.

When x is different from 0, the compounds of Formula (I) bear free alcoholic groups.

Preferably, in Formula (I) A is $CHR_3$, O, more preferably A is $CHR_3$.

Preferably, in Formula (I) x is from 0 to 6, more preferably 1 to 4.

G may comprise monomeric, oligomeric and polymeric polyols and mixtures thereof, and/or alcoxylated moieties and mixture thereof, optionally comprising amino, ester or amido groups.

According to another embodiment, the invention relates to a compound of formula (II)

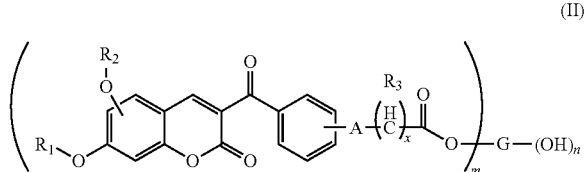   (II)

wherein
G is a residue of the multifunctional compound (core) $G$—$(OH)_{m+n}$; m and n are both integer numbers and m+n is comprised between 2 and 10;
m is comprised between 2 and 8;
x is an integer number comprised between 0 and 10, when x is 0 A is directly linked to the carbonyl group;
A represents independently one of one another $CHR_3$, O, S, $NR_4$ where $R_4$ is an alkyl $C_1$-$C_6$ group;
$R_3$ is hydrogen, alkyl $C_1$-$C_{12}$, substituted or unsubstituted phenyl, aryl or heteroaryl, cycloalkyl $C_5$-$C_6$, alkyl $C_1$-$C_{12}$ which is substituted with SH, —N(alkyl $C_1$-$C_6$)$_2$, piperidino, morpholino, piperazino, —OH, —O(alkyl $C_1$-$C_{12}$), —COOH, or $C_1$-$C_{12}$ alkoxy.
$R_1$, $R_2$ are each independently, alkyl $C_1$-$C_{12}$, substituted or unsubstituted phenyl, aryl or heteroaryl, cycloalkyl $C_5$-$C_6$, alkyl $C_1$-$C_{12}$ which is substituted with SH, —N(alkyl $C_1$-$C_6$)$_2$, piperidino, morpholino, piperazino, —OH, —O(alkyl $C_1$-$C_{12}$), —COOH; or $C_1$-$C_{12}$ alkoxy; with the proviso that the photoinitiators of Formula (II) do not contain photocurable ethylenically unsaturated groups.

Preferably, in Formula (II) m+n is comprised between 2 and 8, and more preferably between 3 and 6.

Preferably, in Formula (II), m is comprised between 3 and 6 and more preferably between 3 and 5.

When n is different from 0, the compounds of Formula (II) have free alcoholic groups.

Preferably, in Formula (II) A is CHR3, O, more preferably A is $CHR_3$.

Preferably, in Formula (II) x is comprised between 0 and 6, more preferably x is comprised between 1 and 4. In Formula (II) of the present disclosure:

$G$—$(OH)_{m+n}$ is a polyhydroxy compound, which can be selected from monomeric, oligomeric and polymeric polyols, and mixture thereof.

Examples of suitable monomeric and oligomeric polyols include glycerol, di-glycerol, tri-glycerol, triethanolamine, trimethylol propane, di-trimethylol propane, pentaerythritol, di-pentaeritrithol, sugar alcohols, such as sorbitol, mannitol and xylitol and mixtures thereof.

Examples of polymeric polyols include alkoxylated compounds, polyhydroxy polyethers, which can be both aliphatic or aromatic, polyhydroxy polyesters, polyhydroxy polyamides, polyhydroxy polyimides, polyhydroxy polycarbonates; styrene-allyl alcohols copolymers.

According to a preferred embodiment, the (poly)hydroxy moiety G is alkoxylated.

Examples of such alkoxylated compounds include monomeric and oligomeric polyols mentioned above, which have been alkoxylated, for example ethoxylated and/or propoxylated and/or butoxylated. Other suitable examples are linear or branched polyamines, which have been alkoxylated, and polyalkoxylated diamines, such as ethoxylated ethylene diamine and ethoxylated 1,3-propylene diamine.

In the alkoxylated compounds of the invention, each group reactive toward the alkylene oxide can bear from 0 to 15 alkoxy units, preferably from 1 to 6 alkoxy units.

In a preferred embodiment G or $G$—$(OH)_{m+n}$ is chosen among monomeric and oligomeric polyols.

In another preferred embodiment G or $G$—$(OH)_{m+n}$ is chosen among monomeric and oligomeric polyols which have been ethoxylated and/or propoxylated.

Preferably, G or $G$—$(OH)_{m+n}$ has a number average molecular weight not greater than 1500, more preferably not greater than 800, and most preferably not greater than 500.

Preferably, G or $G$—$(OH)_{m+n}$ is chosen among glycerol, ethoxylated and/or propoxylated glycerol, di-glycerol, ethoxylated and/or propoxylated di-glycerol, trimethylolpropane, ethoxylated and/or propoxylated trimethylolpropane, di-trimethylolpropane, ethoxylated and/or propoxylated di-trimethylolpropane, penthaerythritol, ethoxylated and/or propoxylated penthaerythritol, di-penthaerythritol, ethoxylated and/or propoxylated di-penthaerythritol, sorbitol, ethoxylated and/or propoxylated sorbitol, triethanolamine, ethoxylated and/or propoxylated triethanolamine.

As said, residue G suitable for the realization of the present invention does not contain photocurable ethylenically unsaturated groups.

Preferably $R_1$, $R_2$ are, each independently, an alkyl $C_1$-$C_{12}$ group, more preferably an alkyl $C_1$-$C_4$ group.

In the present description, the expressions "alkyl" or "alkyl group" mean, where not differently indicated, a linear or branched, saturated, $CH_3$ through $C_{12}H_{25}$ alkyl chain and includes all possible variants for each number of carbon atoms in the alkyl group i.e. for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethylpropyl and 2-methyl-butyl, etc.

The expressions "cycloalkyl" or "cycloalkyl group" mean, where not differently indicated, an aliphatic ring containing from 5 to 6 carbon atoms which can be, for instance, cyclopentyl, cyclohexyl.

The expressions "aryl" or "aryl group" include, among others, substituted or unsubstituted phenyl group, substituted or unsubstituted naphthyl group, anthracenyl group, indenyl group, fluorenyl group.

The expressions "heteroaryl" or "heteroaryl group" include, among others, furan, thiophene, pyrrole, oxazole, isooxazole, thiazole, isothiazole, imidazole, pyrazole, pyrane, pyridine, pyrrolidine, piperidine, indole, quinoline, isoquinoline, xanthene, carbazole, acridine, indoline, julolidine.

The term "substituted" means that one or more substituents are present; said substituents include, among others, halogen atoms such as fluorine atom, chlorine atom, bromine atom, iodine atom; an alkyl, cycloalkyl, alkoxy, alkylamino, dialkylamino, aryl, alkylthio or arylthio group and heterocyclic groups.

Preferably, said substituents are selected from methyl, ethyl, isopropyl, tert-butyl, phenyl, trifluoromethyl, cyano, acetyl, ethoxycarbonyl, carboxyl, carboxylate, amino, methylamino, dimethylamino, ethylamino, diethylamino, isopropylamino, diisopropylamino, cyclohexylamino, dicyclohexylamino, acetylamino, piperidino, pyrrolidyl, methoxy, ethoxy, propoxy, isopropoxy, butoxy, pentyloxy, phenoxy, hydroxyl, acetoxy, —$PO_3H$, methylthio, ethylthio, i-propylthio, n-propylthio, phenyltio, mercapto, acetylthio, thiocyano, methylsulfinyl, methylsulfonyl, dimethylsulfonyl, sultanate groups, trimethylsilyl, triethylsilyl, trimethylstannyl, furyl, thienyl, pyridyl, piperidino, morpholino and pyrrolidyl groups.

According to a preferred embodiment, $R_1$ and $R_2$ are the same $C_1$-$C_4$ alkyl, advantageously methyl. According to a preferred embodiment, $OR_2$ is in 5-position.

According to a preferred embodiment, A is in 4-position (para-position respect to the carbonyl group).

Preferably $R_3$ is hydrogen.

According to a preferred embodiment, $R_1$, $R_2$, $R_3$ and A have the same meaning in each "m" occurrence, i.e. the two or more 3-ketocoumarin moieties are the same in any single compound of Formula (I).

In a preferred embodiment
G is chosen among monomeric and oligomeric polyols which have been ethoxylated and/or propoxylated;
$R_1$, $R_2$ are, each independently, an alkyl $C_1$-$C_{12}$ group, more preferably an alkyl $C_1$-$C_4$ group, especially methyl;
$R_3$ is hydrogen;
$OR_2$ is in 5-position; and
A is in 4-position.

The compounds represented by Formula (I) and of formula (II) can be prepared according to conventional methods known to the skilled in the art. For example, compounds of Formula (I) may be prepared by transesterification

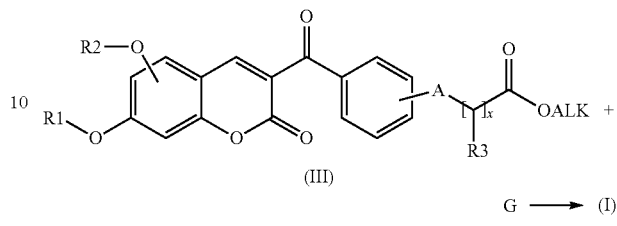

And similarly for formula (II):

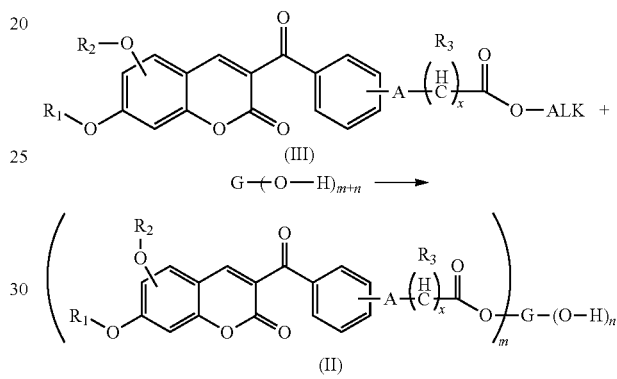

wherein ALK is an alkyl group, for example methyl or ethyl, and G is as described above.

The compounds of Formula (III) can be prepared according to known procedures.

More details relating to the synthesis of representative compounds of the invention are reported in the Experimental Section of the present description.

The process for the preparation of compounds of Formula (I) and (II) described above is a further subject-matter of the invention. Other synthesis routes can anyway be used.

The compounds of Formula (I) and (II) are useful as photoinitiators. The use of the compounds of Formula (I) and (II) as photoinitiators in photopolymerization processes is a further aspect of the present invention, as well as a method for light curing which comprises using the compounds of Formula (I) and (II) as photoinitiators.

the term "photoinitiator" means a molecule that possesses a functional group able to generate radicals (alone or in combination with a co-initiator) capable of starting a polymerization upon exposure to light with an appropriate wavelength. Said compositions constitute a further subject-matter of the invention.

Compounds of Formula (I) and (II) are useful, in particular, in photopolymerizable compositions suitable for inks and coatings that can be photopolymerized by exposure to a radiation source.

For their use, compounds of Formula (I) and (II) are included in photopolymerizable compositions which comprise at least one ethylenically unsaturated compound and at least one compound of Formula (I) and (II). The expression "ethylenically unsaturated compound" indicates a monomer, oligomer or prepolymer having at least one unsaturated double bond, or a mixture thereof, capable of undergoing radical polymerization. Also monomers, oligomers and prepolymers combinations with different degrees of unsaturation can be used.

The monomers suitable for the realization of the present invention are those commonly used in the field and can be chosen, for example, among vinyl ethers, N-vinyl pyrrolidone, N-vinyl caprolactam, mono- and poly-functional allyl ethers such as trimethylol propane diallyl ether, styrenes and alpha-methyl styrenes, esters of (meth)acrylic acid with aliphatic alcohol, glycols, polyhydroxylated compounds such as pentaerythritol or trimethylol propane, esters of vinyl alcohol with acrylic or aliphatic acid, derivatives of fumaric and maleic acids.

Suitable oligomers or prepolymers for the present invention comprise, for example, polyesters, polyacrylates, polyurethanes, epoxy resins, polyethers with acrylic, maleic or fumaric functionalities.

Monomers, oligomers and prepolymers, which are commonly used in photopolymerizable ink are preferred. These compounds are well known to the skilled in the art and are described for example in WO2014/063997.

The photocurable compositions of the present invention preferably comprise from 50 to 99.9% by weight, of at least one ethylenically unsaturated compound and from 0.1 to 35% by weight of a compound of Formula (I) and/or (II).

More preferably, the photocurable compositions of the present invention comprise from 70 to 98.9% by weight, of at least one ethylenically unsaturated compound and from 0.1 to 20% by weight of a compound of Formula (I) or (II), more preferably from 0.2 to 15% by weight.

Unless indicated otherwise, the expression "by weight means that the value are expressed as percentage weight with respect to the total weight of the composition.

Besides the above-mentioned compounds, other components normally used in the field and known to the experts in the art can be added to the photopolymerizable compositions of the invention. For example, thermal stabilizers, photo-oxidation stabilizers, anti-oxidants, fillers, dispersants, coloring and/or opacifying substances and other additives of general use. Others components of the photopolymerizable compositions of the invention can be non-photopolymerizable polymers present as chemically inert substances, as an example nitrocellulose, polyacrylic esters, polyolefins, etc.

The photopolymerizable compositions of the invention can also conveniently include a co-initiator, which is a molecule that acts as hydrogen donor that increases the polymerization rate. The co-initiators are known in the art and they are typically alcohols, thiols, amines or ethers that have an available hydrogen, bonded to a carbon adjacent to the heteroatom. Such co-initiators are generally present in an amount comprised between 0.2 and 15% by weight, preferably from 0.2 to 8% by weight. Suitable co-initiators include, but are not limited to, aliphatic, cycloaliphatic, aromatic, aryl-aliphatic, heterocyclic, oligomeric or polymeric amines. They can be primary, secondary or tertiary amines, for example butyl amine, dibutyl amine, tributyl amine, ciclohexyl amine, benzyldimethyl amine, di-cyclohexyl amine, N-phenyl glycine, triethyl amine, phenyl-diethanol amine, triethanolamine, piperidine, piperazine, morpholine, pyridine, quinoline, esters of dimethylamino benzoic acid, Michler's ketone (4,4'-bis-dimethyl aminobenzophenone) and corresponding derivatives.

As the amine co-initiator, an amine-modified acrylate compound can be used, examples of such amine-modified acrylate include acrylates modified by reaction with a primary or secondary amine that are described in U.S. Pat. No. 3,844,916, EP 280222, U.S. Pat. Nos. 5,482,649, 5,734,002 or US2013/0012611. Preferred co-initiators are Esacure A198 (bis-N,N-[4-dimethylaminobenzoyl) oxyethylen-1-yl]-methylamine), Esacure EDB (ethyl-4-dimethylamino benzoate) and Photomer 4250 all commercialized by IGM Resins B. V., 2-ethylhexyl-4-dimethylaminobenzoate and N-phenyl glycine.

The photopolymerizable compositions of the invention can also conveniently include other photoinitiators commonly used in the field.

Other photoinitiators, co-initiators and further components that may be comprised in the composition of the invention are described for example in the document WO2014/063997 mentioned above.

The use of the compounds of Formula (I) and of formula (II), below, as photoinitiators, individually or in admixture with each other, or in admixture with other photoinitiators or co-initiators, represents a further subject-matter of the invention.

According to a particularly preferred aspect of the invention the compounds of Formula (I) or (II) are used as sensitizers of sensitizable photoinitiators in photopolymerizable compositions.

For "sensitizer" or "sensitizer agent" is meant a molecule that, by an energy transfer process, activates a photoinitiator at a wavelength at which the photoinitiator alone would not be reactive.

The use of the compounds of Formula (I) and of formula (II) as sensitizers, individually or in admixture with each other, or in admixture with other sensitizers, represents a further subject-matter of the invention.

In this case, the photopolymerizable composition may comprise from 70 to 98.9% by weight of at least one photopolymerizable compound, from 0.1 to 10% by weight of at least one compound of Formula (I) or (II), as sensitizer and from 1 to a 15% by weight at least one sensitizable photoinitiator, for example a ketosulfone, an α-aminoketone or a cationic photoinitiator such as a sulphonium salt, a thianthrenium salt or a iodonium salt and, optionally, from 0.2 to 8% by weight of a co-initiator. The preferred sensitizable photoinitiator are selected from 1-[4-[(4-benzoyl-phenyl)-thio]-phenyl]-2-methyl,2-[(4-methyl-phenyl)-sulfonyl]-propan-1-one (Esacure 1001, from IGM Resins B. V.), 2-methyl-1-(4-methylthiophenyl)-2-morpholinopropane-1-one), 2-benzyl-2-dimethylamino-1-(4-morpholinophenyl)-butan-1-one, (2-(dimethylamino)-2-[(4-methylphenyl)methyl]-1-[4-(4-morpholinyl)phenyl]-1-butanone), diphenyl-(4-phenylthio)-phenylsulphonium hexafluoroantimonate) and thio-di-1,4-phenylene-bis(diphenylsulphonium) hexafluoroantimonate mixed salts, diphenyl-(4-phenylthio)-phenylsulphonium hexafluorophosphate and thio-di-1,4-phenylene-bis(diphenylsulphonium) hexafluorophosphate mixed salts, thio-di-1,4-phenylene-bis (diphenylsulphonium) hexafluorophosphate, di-(4-methylphenyl)4-(4-methylphenylthio)phenylsulphonium hexafluoroantimonate and thio-di-1,4-phenylene-bis[di-(4-methylphenyl)sulphonium]hexafluoroantimonate mixed salts, di-(4-methylphenyl)4-(4-methylphenylthio)phenylsulphonium hexafluorophosphate and thio-di-1,4-phenylene-bis[di-(4-methylphenyl)sulphonium]hexafluorophosphate mixed salts, thio-di-1,4-phenylene-bis[di-(4-hydroxyethoxyphenyl)sulphonium]hexafluorophosphate, thio-di-1,4-phenylene-bis[di-(4-hydroxyethoxyphenyl)sulphonium] hexafluoroantimonate, 10-biphenyl-4-yl-2-isopropyl-9-oxo-9H-thioxanthen-10-ium hexafluorophosphate and solution thereof, 9-(4-hydroxyethoxyphenyl)thianthrenium hexafluorophosphate, diphenyliodonium hexafluorophosphate, (4-octyloxyphenyl)phenyliodonium hexafluoroantimonate, {4-[2-hydroxy-tetradecypoxy]phenyl}-phenyliodonium hexafluoroantimonate, bis-(4-methylphenyl)iodonium hexafluorophosphate and solution thereof, 4-isobutylphenyl-4'-methylphenyliodonium hexafluorophosphate, bis-(4-hexafluoroantimonate, bis-(4-dodecylphenyl)iodonium tetrakis-(pentafluorophenyl)borate, tolylcumyliodonium tetrakis-(pentafluorophenyl)borate and 4-isopropylphenyl-4'-methylphenyl iodonium hexafluorophosphate.

It has been surprisingly observed that compounds of Formula (I) and (II) show a relatively high the functionality per gram and the relatively small core molecular weight renders the material highly soluble in photocurable compositions, especially in photocurable coating compositions. In this role, said compounds improve the reactivity of the primary cationic photoinitiators. Most notably, said primary cationic photoinitiators are triaryl sulfonium salts and diaryl iodonium salts (Chemistry & Technology of UV&EB Formulation for Coatings, Inks & Paints vol. III, p 420 and 395 respectively).

Particularly preferred are the iodonium salts.

Ccompounds of Formula (I) and (II) work both in transparent photopolymerizable compositions and in non-transparent or colored compositions and, in particular, are useful for the preparation of photopolymerizable inks. The photoinitiators and the compositions of the invention are particularly suited for the preparation of photopolymerizable inks for ink-jet printing.

For this reason, the photopolymerizable composition of the invention can further comprise from 0.01 to 30% by weight of colorants.

Colorants which can be used in the photopolymerizable inks of the invention are dyes, pigments or a combination thereof. Organic and/or inorganic pigments may be used. The colorants are preferably pigments or polymeric dyes, most preferably pigments. The pigments may be black, white, cyan, magenta, yellow, red, orange, violet, blue, green, brown, mixtures thereof, and the like, as well as other conventional pigments, well known to the skilled in the art, Exemplary organic pigments include insoluble azo pigments, condensed azo pigments, azo lake, and chelate azo pigments; polycyclic pigments, such as phthalocyanine pigments, perylene and perinone pigments, anthraquinone pigments, quinacridone pigments, dioxane pigments, thioindigo pigments, isoindolinone pigments, and quinophthalone pigments; dye chelates, such as basic dye chelates and acid dye chelates; dye lakes, such as basic dye lakes and acid dye lakes; and nitro pigments, nitroso pigments, aniline black, and fluorescent pigments.

For photopolymerizable white inks, the white colorants are preferably present in an amount of 3% to 30% by weight of the ink composition, and more preferably 5% to 25%. Usually the other colorants are present in the photopolymerizable inks of the invention in the range of 0.01 to 10% by weight, preferably in the range of 0.1 to 5% by weight.

Colorants for ink-jet printing are particularly preferred.

In addition to the main components, the photopolymerizable inks can contain also other specific ingredients such as co-initiators and other photoinitiators, such as those described in the preceding paragraphs and in the same amount, dispersants, surfactants and other additives which are well known to the expert in the art. Said components are described for example in WO2014/063997.

It has been surprisingly observed that compounds of Formula (I) and (II) show a relatively high the functionality per gram and the relatively small core molecular weight renders the material highly soluble in photocurable compositions, especially in photocurable coating compositions. In this role, said compounds improve the reactivity of the primary cationic photoinitiators. Most notably, said primary cationic photoinitiators are triaryl sulfonium salts and diaryl iodonium salts (Chemistry & Technology of UV&EB Formulation for Coatings, Inks & Paints vol. III, p 420 and 395 respectively).

The compositions and the inks described above are also subject-matter of the present invention.

According to another of its aspects, it is a further subject-matter of the invention a process for photocuring photopolymerizable compositions and inks, which process comprises:

I) preparing a photopolymerizable composition comprising:
 a) from 50 to 99.9% by weight, preferably from 70 to 98.9% by weight, of at least one ethylenically unsaturated compound;
 b) from 0.1 to 35% by weight, preferably from 0.1 to 20% by weight, and more preferably from 0.2 to 15% by weight of at least one compound of Formula (I), as defined above;
II) photopolimerizing the composition of step I with a light source.

The photocuring compositions and the inks comprising the compounds of formula (I) and (II) also represent a subject-matter of the present invention.

Accordingly, a large number of the most varied kinds of light source may be used, the light source emits at wavelengths comprised from approximately 200 nm to approximately 600 nm. Both point sources and planiform radiators (lamp carpets) are suitable. Examples are: carbon arc lamps, xenon arc lamps, medium pressure, high pressure and low pressure mercury arc radiators, doped, where appropriate, with metal halides (metal halide lamps), microwave-excited metal vapour lamps, excimer lamps, superactinic fluorescent tubes, fluorescent lamps, argon incandescent lamps, flash lamps, photographic floodlight lamps, light-emitting diodes (LED), electron beams, X-rays and lasers. The distance between the lamp and the substrate according to the invention to be exposed may vary according to the intended use and the type and strength of the lamp and may be, for example, from 1 cm to 150 cm. Particularly preferred are LED light source emitting at wavelengths comprised between 365 nm and 420 nm, preferably 365 nm, 385 nm and 395 nm.

Optionally, said photopolymerizable composition may be applied to a substrate prior to carrying out the photopolymerization step with said light source. Examples of substrates include but are not limited to polyethylene, polypropylene, polyester terephthalate, nylon, paper, board, wood, metal and glass, and other substrates well known to those skilled in the art. Examples of application processes include but are not limited to printing by flexography, gravure, screen, ink jet, lithography, or intaglio, coating by spray, airless spray, roilcoat, flexography, gravure, curtain, cascade, slot, brush and wire-wound roller. Other methods of applying said photopolymerizable composition will be apparent to those skilled in the art. Said photopolymerizable composition may also be applied over a substrate already comprising a coated or printed layer. Said photopolymerizable composition may, after photopolymerization with said light source, be overprinted or overcoated with one or more compositions suitable for printing or coating.

The article obtained by applying said photopolymerizable composition to said substrate by said means of coating or printing, and photopolymerizing by said light source, with or without further elaboration of the article by further coating or printing, is a further object of the invention.

According to a preferred embodiment, in the photopolymerizing process, the compound of Formula (I) or (II) is defined as in the preferred embodiments above disclosed.

It has been observed that the compounds of Formula (I) and (II) overcome the drawbacks of the prior art, as they show an absorbance region between 365 and 420 nm and therefore can be used as photoinitiators by LED lamps, do not provoke yellowing, have a good photochemical reactivity and solubility do not generate bad smelling degradation product and are safe for health and environment.

Moreover, we found that compound described in the example 4 showed a reactivity superior to the compound described in WO2014/018826 example 18 when used in the same weight amount, with mercury lamp and LED lamps both in clear and pigmented systems.

EXPERIMENTAL SECTION AND EXAMPLES

Example 1

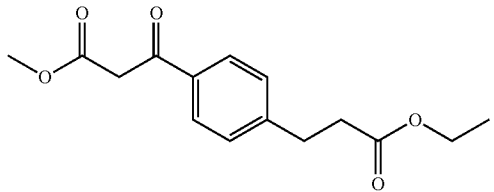 [SMILES: CCOC(=O)CCc1ccc(C(=O)CC(=O)OC)cc1]

Under nitrogen atmosphere 67.0 g (502.5 mmol) of aluminum chloride were added in small portions under stirring at 0° C. to a solution of 30.0 g (168.3 mmol) of ethyl 3-phenylpropionate and 24.0 g (175.8 mmol) of methyl 3-chloro-3-oxopropionate in 250 mL of dichloromethane. After stirring at room temperature for 4 hours, the reaction was poured in ice and water and the resulting mixture was kept under stirring for 30 minutes. Then the organic phase was separated, washed with water, dried over sodium sulphate, filtered and the solvent removed by distillation under vacuum obtaining 37.7 g of a yellow oil (yield 80%).

$^1$H-NMR (CDCl$_3$, δ ppm): 1.22 (t, 3H), 2.65 (t, 2H), 3.05 (t, 2H), 3.75 (s, 3H), 3.98 (s, 2H), 4.10 (q, 2H), 7.30 (d, 2H), 7.85 (d, 2H).

Example 2

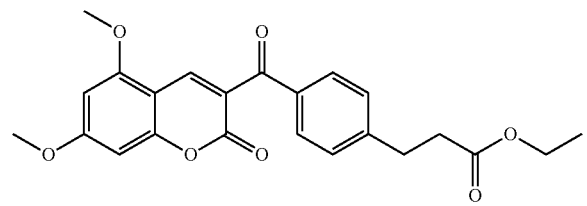 [SMILES: CCOC(=O)CCc1ccc(C(=O)c2cc3c(OC)cc(OC)cc3oc2=O)cc1]

34.1 g (122.5 mmol) of Example 1 and 0.86 g (10.1 mmol) of piperidine were added to a solution of 22.3 g (122.4 mmol) of 4.6-dimethoxy-2-hydroxy-benzaldehyde in 100 mL of ethanol. The mixture was stirred for 2 hours under reflux, then cooled to room temperature. The reaction product was recovered by filtration obtaining 25.0 g of a white-yellow solids (yield 50%).

$^1$H-NMR (CDCl$_3$, δ ppm): 1.23 (t, 3H), 2.65 (t, 2H), 3.10 (t, 2H), 3.89 (m, 6H), 4.12 (q, 2H), 6.30 (d, 1H), 6.45 (d, 1H), 7.30 (d, 2H), 7.79 (d, 2H), 8.40 (s, 1H).

Example 3

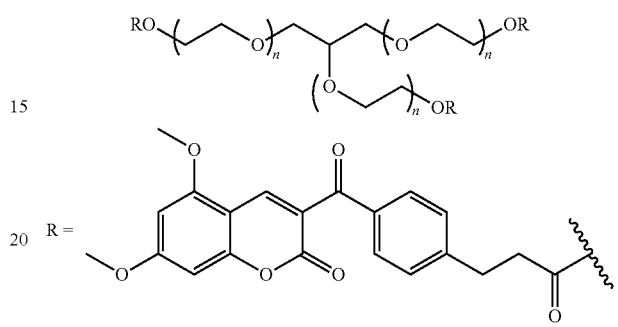

0.25 g (1.20 mmol) of butyltin hydroxide oxide hydrate were added in small portions under stirring at 150° C. to a mixture of 1.00 g (2.44 mmol) of Example 2 and 0.37 g (hydroxyl n° 370/g) of Rolfor GL/609 (purchased from Lamberti SpA). The mixture was stirred at 150° C. for 24 hours eliminating ethanol by distillation. After cooling to room temperature, the reaction mixture was dissolved in dichloromethane and filtered. The filtrate was washed with water, dried over sodium sulphate and the solvent removed by distillation under vacuum. The crude product was purified by flash column chromatography on silica gel (dichloromethane:methanol 95:5) obtaining 0.79 g of a yellow-brown oil (yield 63%).

$^1$H-NMR (CDCl$_3$, δ ppm): 2.65 (m, 6H), 3.00 (m, 6H), 3.45-3.75 (m, 49H), 3.90 (s, 18H), 4.20 (m, 6H), 6,30 (s, 3H), 6.45 (s, 3H), 7.30 (d, 6H), 7.75 (d, 6H), 8.40 (m, 3H).

Example 4

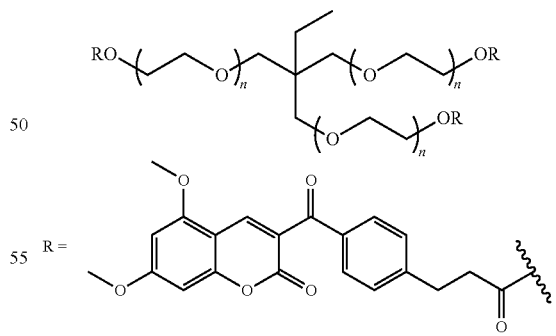

0.51 g (2.44 mmol) of butyltin hydroxide oxide hydrate were added in small portions under stirring at 150° C. to a mixture of 2.00 g (4.87 mmol) of Example 2 and 0.75 g (hydroxyl n° 364/g) of polyhol 3380 (purchased from Perstorp). The mixture was stirred at 150° C. for 40 hours eliminating ethanol by distillation. After cooling to room temperature, the reaction mixture was dissolved in dichloromethane and filtered. The filtrate was washed with water, dried over sodium sulphate and the solvent removed by distillation under vacuum. The crude product was purified by flash column chromatography on silica gel (dichloromethane:methanol 95:5) obtaining 2.00 g of a yellow-brown oil (yield 79%).

$^1$H-NMR (CDCl$_3$, δ ppm): 0.80 (m, 3H), 1.45 (m, 2H), 2.65 (m, 6H), 3.00 (m, 6H), 3.35-3.70 (m, 38H), 3.90 (s, 18H), 4.20 (m, 6H), 6.30 (s, 3H), 6.45 (s, 3H), 7.30 (d, 6H), 7.75 (d, 6H), 8.40 (m, 3H).

Example 5

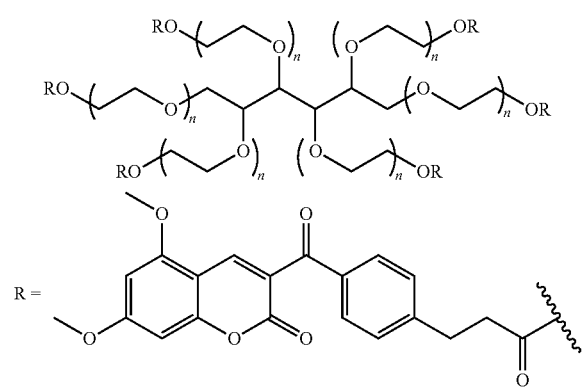

0.51 g (2.44 mmol) of butyltin hydroxide oxide hydrate were added in small portions under stirring at 150° C. to a mixture of 2.00 g (4.87 mmol) of Example 2 and 0.91 g (hydroxyl n° 300/g) of sorbilene RE/20 (purchased from Lamberti SpA). The mixture was stirred at 150° C. for 32 hours eliminating ethanol by distillation. After cooling to room temperature, the reaction mixture was dissolved in dichloromethane and filtered. The filtrate was washed with water, dried over sodium sulphate and the solvent removed by distillation under vacuum. The crude product was purified by flash column chromatography on silica gel (dichloromethane:methanol 95:5) obtaining 0.98 g of a yellow-brown oil (yield 36%).

$^1$H-NMR (CDCl$_3$, δ ppm): 2.65 (m, 12H), 3.00 (m, 12H), 3.50-3.75 (m, 100H), 3.90 (m, 36H), 4.20 (m, 12H), 6.30 (m, 6H), 6.45 (m, 6H), 7.30 (m, 12H), 7.75 (m, 12H), 8.40 (m, 6H).

Example 6

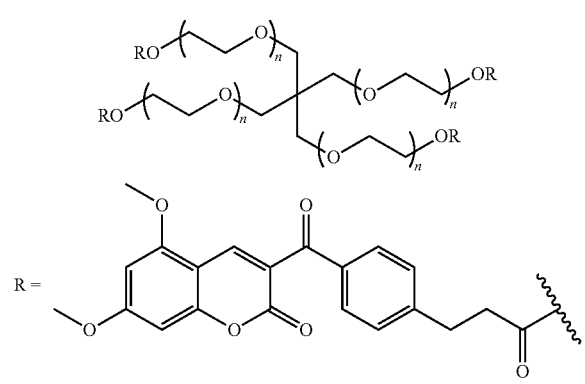

n=0.51 g (2.44 mmol) of butyltin hydroxide oxide hydrate were added in small portions under stirring at 150° C. to a mixture of 2.00 g (4.87 mmol) of Example 2 and 0.43 g (hydroxyl n° 642/g) of pentaeritrite 5 EO (purchased from Lamberti SpA). The mixture was stirred at 150° C. for 44 hours eliminating ethanol by distillation. After cooling to room temperature, the reaction mixture was dissolved in dichloromethane and filtered. The filtrate was washed with water, dried over sodium sulphate and the solvent removed by distillation under vacuum. The crude product was purified by flash column chromatography on silica gel (dichloromethane:methanol 95:5) obtaining 1.07 g of a yellow-brown oil (yield 49%).

$^1$H-NMR (CDCl$_3$, δ ppm): 2.65 (m, 8H), 3.00 (m, 8H), 3.25-3.75 (m, 22H), 3.90 (m, 24H), 4.10-4.25 (m, 8H), 6.30 (m, 4H), 6.45 (m, 4H), 7.30 (m, 8H), 7.75 (m, 8H), 8.40 (m, 4H).

Example 7

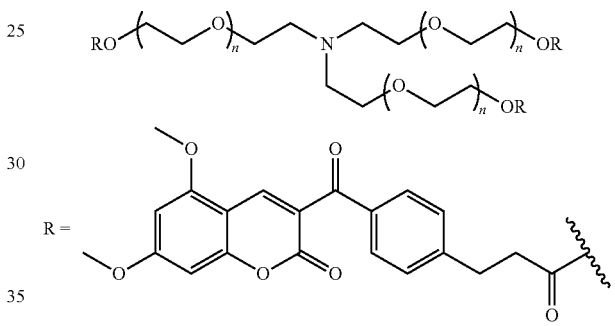

n=1.35 g (6.47 mmol) of butyltin hydroxide oxide hydrate were added in small portions under stirring at 100° C. to a mixture of 2.00 g (4.87 mmol) of Example 2 and 0.45 g (1.61 mmol) of triethanolamine ethoxylate 1 EO/OH (purchased from Sigma Aldrich) in 5 mL of p-xylene. The mixture was stirred for 24 hours under reflux eliminating ethanol by distillation. After cooling to room temperature, the reaction mixture was diluted with dichloromethane and filtered. The filtrate was washed with 1 M sodium hydrogen carbonate aqueous solution and then with water. The organic phase was dried over sodium sulphate and the solvent removed by distillation under vacuum. The crude product was purified by flash column chromatography on silica gel (dichloromethane:methanol 95:5) obtaining 0.90 g of a yellow-brown oil (yield 40%).

$^1$H-NMR (CDCl$_3$, δ ppm):2.51-3.10 (m, 18H), 3.28-3.66 (m, 11H), 3.88 (m, 18H), 4.05-4.31 (m, 6H), 6.27-6.33 (m, 3H), 6.42-6.49 (m, 3H), 7.28-7.33 (m, 6H), 7.71-7.82 (m, 6H), 8.34-8.45 (m, 3H)

Example 8

Comparative Tests

The 3-ketocoumarins of the invention, were compared with Omnipol TX (IGM Resins B. V.) (COMP-1) and the 3-ketocoumarins of the prior art prepared as described in WO2014018826 Example 9 (COMP-2) and Example 18 (COMP-3).

Example 8.1

Reactivity Test

Example 8.1.1

Clear Formulation

The photopolymerizable compositions for the test were prepared dissolving the photoinitiators and the co-initiator, Esacure EDB (IGM Resins 8.V.), at a concentration of 3% by weight (wt) each in a mixture 99.5:0.5 wt of Ebecryl 605 and Ebecryl 350 (Allnex).

The photopolymerizable compositions placed in the sample lodgment of a FT-IR (FT-IR 430-Jasco), were exposed to two different sources:
1) a LED source (400 nm) located at a distance of 25 mm from the sample and at an angle of 30°. (Table 1)
2) A Mercury lamp (160 W) located at a distance of 65 mm from the sample and at an angle of 30°. (Table 2)

IR spectra were acquired at constant time intervals during the photopolymerization and the reduction over the time of the area of the peaks at 1408 and 810 $cm^{-1}$ assigned to the acrylic double bonds was determined using the IR software.

This allows quantifying the degree of polymerization and therefore the efficiency of the photoinitiator.

The results at 400 nm, expressed as percent of polymerization over the time, are reported in Table 1 and the results with the Mercury lamp are reported in Table 2.

TABLE 1

| Example | 0.5 sec | 2 sec |
| --- | --- | --- |
| Ex. 3 | 73 | 82 |
| Ex. 4 | 71 | 82 |
| Ex. 5 | 64 | 77 |
| Ex. 6 | 72 | 85 |
| Ex. 7 | 60 | 63 |
| COMP-1 | 66 | 79 |
| COMP-2 | 39 | 56 |
| COMP-3 | 35 | 46 |

TABLE 2

| Example | 0.2 sec | 1 sec |
| --- | --- | --- |
| Ex. 3 | 61 | 69 |
| Ex. 4 | 63 | 70 |
| Ex. 5 | 62 | 69 |
| Ex. 6 | 62 | 69 |
| Ex. 7 | 61 | 70 |
| COMP-1 | 43 | 63 |
| COMP-2 | 53 | 63 |
| COMP-3 | 52 | 62 |

Example 8.1.2

Cyan Inkjet Ink

The photopolymerizable compositions for the test were prepared by dissolving the photoinitiators and the co-initiator Esacure EDB at a concentration of 5.0% wt each in a cyan ink for ink-jet printing.

The photopolymerizable compositions placed in the sample lodgment of a FT-IR (FT-IR 430-Jasco), were exposed to two different sources:
1) a LED source (400 nm) located at a distance of 25 mm from the sample and at an angle of 30°, (Table 3)
2) A Mercury lamp (160 W) located at a distance of 65 mm from the sample and at an angle of 30°. (Table 4)

IR spectra were acquired at constant time intervals during the photopolymerization and the reduction over the time of the area of the peaks at 1408 $cm^{-1}$ and 810 $cm^{-1}$ assigned to the acrylic double bonds was determined using the IR software. This allows quantifying the degree of polymerization and therefore the efficiency of the photoinitiator.

The results at 400 nm, expressed as % of polymerization over the time, are reported in Table 3 and the results with the Mercury lamp are reported in Table 4.

TABLE 3

| Example | 0.5 sec | 2 sec |
| --- | --- | --- |
| Ex. 3 | 65 | 76 |
| Ex. 4 | 67 | 80 |
| Ex. 5 | 64 | 76 |
| Ex. 6 | 64 | 77 |
| Ex. 7 | 56 | 69 |
| COMP-1 | 53 | 79 |
| COMP-2 | 34 | 57 |
| COMP-3 | 29 | 55 |

TABLE 4

| Example | 1 sec | 6 sec |
| --- | --- | --- |
| Ex. 3 | 60 | 89 |
| Ex. 4 | 60 | 90 |
| Ex. 5 | 59 | 89 |
| Ex. 6 | 49 | 90 |
| Ex. 7 | 66 | 96 |
| COMP-1 | 12 | 32 |
| COMP-2 | 37 | 80 |
| COMP-3 | 28 | 67 |

These tests confirm that compounds of Formula (I) and (II) are more reactive than the comparatives (COMP-1, COMP-2, COMP-3).

The invention claimed is:

1. A compound of formula (II)

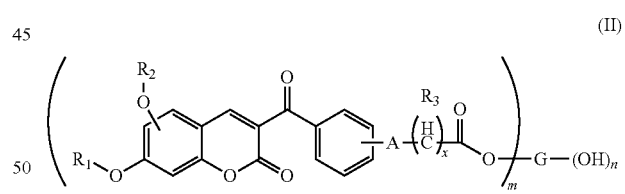

wherein
G is a residue of the multifunctional compound (core) G—$(OH)_{m+n}$;
m and n are both integer numbers and m+n is comprised between 2 and 10;
m is comprised between 2 and 8;
x is an integer number comprised between 0 and 10, when x is 0 A is directly linked to the carbonyl group;
A represents independently one of one another CHR3, O, S, NR4 where R4 is an alkyl $C_1$-$C_6$ group;
R3 is hydrogen, alkyl $C_1$-$C_{12}$, substituted or unsubstituted phenyl, aryl or heteroaryl, cycloalkyl $C_5$-$C_6$, alkyl $C_1$-$C_{12}$ which is substituted with SH, —N(alkyl $C_1$-$C_6$)$_2$, piperidino, morpholino, piperazino, —OH, —O(alkyl COOH, or $C_1$-$C_{12}$ alkoxy;

$R_1$, $R_2$ are each independently, alkyl $C_1$-$C_{12}$, substituted or unsubstituted phenyl, aryl or heteroaryl, cycloalkyl $C_5$-$C_6$, alkyl $C_1$-$C_{12}$ which is substituted with SH, —N(alkyl $C_1$-$C_6$)$_2$, piperidino, morpholino, piperazino, —OH, —O(alkyl $C_1$-$C_{12}$), —COOH; or $C_1$-$C_{12}$ alkoxy;

with the proviso that the photoinitiators of Formula (II) do not contain photocurable ethylenically unsaturated groups.

2. The compound of Formula (II) according to claim 1, wherein m is from 3 to 6.

3. The compound of Formula (II) according to claim 1, wherein x is from 0 to 6.

4. The compound of Formula (II) according to claim 1, wherein x is from 1 to 4.

5. The compound of Formula (II) according to claim 1, wherein A is $CH_2$.

6. The compound of Formula (II) according to claim 1, wherein G is chosen among monomeric and oligomeric polyols comprising ethoxylated and/or propoxylated moeties.

7. The compound of Formula (I) according to claim 1, wherein $R_1$ and $R_2$ are both a methyl group.

8. The compound of (II) according to claim 1, wherein $R_3$ is hydrogen.

9. A method for light curing which comprises using the compound of Formula (II) according to claim 1 as photoinitiators in an ultraviolet light or blue light induced photopolymerization processes.

10. The method according to claim 9, wherein said polymerization processes are for inkjet printing inks.

11. The method according to claim 9, wherein said compound of Formula (II) is, in combination with at least one co-initiator.

12. The method according to claim 11, wherein the co-initiator is an amine.

13. The method according to claim 12 wherein the co-initiator is an amine comprising an unsaturated ethylenic moiety.

14. A photopolymerizable composition, a photopolymerizable ink or a photopolymerizable coating, which comprises at least one compound of Formula (II) as defined in claim 1, optionally in combination with at least one co-initiator.

* * * * *